(12) United States Patent
De Bruijn et al.

(10) Patent No.: US 8,071,083 B2
(45) Date of Patent: Dec. 6, 2011

(54) TISSUE REGENERATION

(75) Inventors: Joost Dick De Bruijn, Amersfoort (NL); Gerrit Jacobus Meijer, Bilthoven (NL)

(73) Assignee: Progentix Orthobiology B.V., Bilthoven (NL)

( * ) Notice: Subject to any disclaimer, the term of this patent is extended or adjusted under 35 U.S.C. 154(b) by 1669 days.

(21) Appl. No.: 11/298,208

(22) Filed: Dec. 8, 2005

(65) Prior Publication Data

US 2006/0136068 A1 Jun. 22, 2006

Related U.S. Application Data

(60) Provisional application No. 60/635,543, filed on Dec. 13, 2004.

(51) Int. Cl.
*C12N 5/0775* (2010.01)
*C12N 5/077* (2010.01)
*A61K 33/42* (2006.01)

(52) U.S. Cl. ........ 424/93.1; 424/422; 424/423; 424/602

(58) Field of Classification Search .................. None
See application file for complete search history.

(56) References Cited

U.S. PATENT DOCUMENTS

| | | | |
|---|---|---|---|
| 6,309,635 B1 * | 10/2001 | Ingber et al. ................ | 424/93.7 |
| 6,541,022 B1 * | 4/2003 | Murphy et al. .............. | 424/422 |
| 2002/0142458 A1 * | 10/2002 | Williams et al. ............ | 435/366 |

OTHER PUBLICATIONS

Retuerto et al., Journal of Thoracic and Cardiovascular Surgery, vol. 127, Issue 4, Apr. 2004, pp. 1041-1050.*
Yu et al., 2009 (Biomaterials, 30, 508-517.*
Meijer et al., 2007 (PLoSMed., 4(2), 0260-0264.*
Stevens et al. (Proc. Nat. Acad Sci. USA, 106(39), 16568-16573 (2009).*
Anderson, "The Cellular Cascades of Wound Healing," *Wound Healing in Bone*, 81-93 (2000).
Davies et al., "Histodynamics of Endosseous Wound Healing," *Bone Formation and Healing*, 1-14 (2000).
Gunatillake et al., "Biodegradable Synthetic Polymers for Tissue Engineering," *European Cells and Materials* 9, 5, 1-16 (2003).
Hillsley et al., "Review: Bone Tissue Engineering: The Role of Interstitial Flow," *Biotechnology and Bioengineering*, 43, 573-581 (1994).
Li et al., "Low-Molecular-Weight Peptides Derived from Extracellular Matrix as Chemoattractants for Primary Endothelial Cells," *Endothelium*, 11, 199-206 (2004).
Nakagawa et al., "Osteoclastogenesis on Tissue-Engineered Bone," *Tissue Engineering*, 10 (1/2), 93-100 (2004).
Qin et al., "Fluid Pressure Gradients, Arising from Oscillations in Intramedullary Pressure, is Correlated with the Formation of Bone and Inhibition of Intracortical Porosity," *Journal of Biomechanics*, 36, 1427-1437 (2003).
Yu et al., "Bioreactor-Based Bone Tissue Engineering: The Influence of Dynamic Flow on Osteoblast Phenotypic Expression and Matrix Mineralization," *PNAS*, 101 (31), 11203-11208 (2004).

* cited by examiner

*Primary Examiner* — Daniel C Gamett
(74) *Attorney, Agent, or Firm* — Leydig, Voit & Mayer, Ltd.

(57) ABSTRACT

The present invention relates to a method of treating a tissue defect in a human or animal body comprising the steps of implanting into said body an unseeded scaffold; allowing or effecting a wound healing response at the site of said defect; allowing said scaffold to be vascularized until a substantially sufficient fluid flow through said scaffold is assured for the transport of nutrients and/or waste products, and seeding said vascularised scaffold with a suitable population of tissue-regenerating cells.

8 Claims, No Drawings

TISSUE REGENERATION

FIELD OF THE INVENTION

The present invention is in the field of tissue engineering. More in particular the invention relates to methods of treating a tissue defect in a human or animal body.

BACKGROUND OF THE INVENTION

The need for replacement tissues and/or organs for the human body, in combination with the shortage of donors has been a strong incentive for the development and production of tissue engineered implants that can take over the function of missing or injured body parts. An advantage of these "engineered" replacement tissues and organs is that they may circumvent many of the hazards and problems associated with donor tissues and organs, and at lower cost. Today, tissue engineering (TE) applications cover virtually every human tissue, including skin, eyes, liver, pancreas, blood vessels, ligaments, cartilage, bone, muscle and parts of the nervous system.

The principle of TE is relatively simple and involves the isolation and culture of cells, and the seeding of the cultured cells onto a biological or artificial scaffold in vitro prior to transplantation of the seeded scaffold into the specific location of the body. The scaffold thereby serves as an attachment matrix and guides the cells during tissue formation or regeneration. The regeneration of the seeded cells into a tissue may take place prior, during or after the implantation. The cells that are used for regenerating a tissue should exhibit an inherent regenerative capacity. Stem cells, that have the ability to differentiate into a variety of different cell types, are now commonly used for this purpose. Stem cells are undifferentiated progenitor cells and may for instance be isolated from autologous sources (patient's bone marrow) and expanded in in vitro culture. Preferred progenitor cells are bone marrow derived mesenchymal stem cells (MSC), that may form connective tissues such as bone, cartilage, tendon, ligament, bone marrow stroma, mucous tissue, fat and muscle. These progenitor cells can be induced by specific bioactive molecules to mature into a required cell type. MSCs may for instance be induced to form osteoblasts by using dexamethasone. Once matured, the cells are then seeded onto the scaffold.

Prior to the implantation of the seeded scaffold in vivo, the seeded cells can be induced by yet other specific bioactive molecules such as growth factors, by ex-vivo gene transfer or by other physical factors to form the required neotissue in vitro. Alternatively, the scaffold comprising the growth factors may be combined with the cells in vivo. An example of the first TE procedure is that of tissue engineering of bone, wherein bone-marrow derived mesenchymal stem cells are expanded, differentiated to bone-forming osteoblasts and subsequently seeded on a biodegradable scaffold. The scaffold is osteoconductive in that it provides a path for the growing bone tissue. The in vitro prepared and loaded scaffold is then implanted in a bone defect and while the seeded cells are induced to form new bone material, the scaffold itself is degraded. An example of the latter TE procedure is that of human articular cartilage repair using the patient's own autologous chondrocytes retrieved at arthroscopy. The chondrocytes are expanded in vitro before being reimplanted into full-thickness articular cartilage defects covered with a sutured and fibrin-glued periosteal patch. Of course, tissues or organs may also be produced completely in vitro and transplanted as ready replacement materials.

Though simple in conception, these procedures can be quite complex in practice. While TE of skin is relatively straightforward due to the 2-D arrangement of cells, the formation of more complex solid structures such as bone and even complete organs is far more demanding, even under controlled in vitro conditions. Bone formation itself preferably occurs in situ since proper bone formation requires that bone is formed in the direction of the functional pressures and is highest in density at high-pressure sites. The compact and spongy material of natural bone is composed such that maximum strength is produced with a minimum of material and, in form and structure, must be formed such that the maximum compressive stresses normally produced by the body weight are resisted in the most economical manner. Moreover, natural formation of bone is the result of the combined action of bone-forming osteoblasts and bone degrading osteoclasts, and the flow of interstitial fluids is believed to play an important role in the activation of the various processes (Hillsley and Frangos, 1994). As a result, functional bone formation cannot properly occur in vitro.

An important problem with in vitro produced TE implants (grafts) is that once the grafts are transplanted in vivo the nutrient supply to the cells is discontinued. Tissues of any size need a blood supply to bring in nutrients and carry out dissimilation products. During the first 6-8 days post transplantation, the vascularization of the implant is the principal factor that limits the viability of the cells. This problem can only partially be addressed by using matrices that house growth factors to stimulate blood vessel ingrowth from the surrounding tissue. Substituting these growth factors with blood-vessel progenitor cells that sprout vessels from within the body of the matrix is one way of enhancing the rate of vascularization. Internally derived vessels then only need to link with surrounding vessels to establish a flow-through circulation. However, because such processes are slow, many of the cells in the implant will have died by then and tissue ingrowth (i.e. ingrowth into the scaffold as to form the 3-D tissue) will be severely hampered.

The possibility of limited tissue ingrowth in tissue-engineered constructs due to insufficient nutrient transport is an important concern in tissue regeneration. Research into the flow velocity around and through scaffolds, as performed with specialized high-aspect-ratio vessel rotating bioreactors and complex three-dimensional (3D) scaffolds for culturing osteoblast cells (Yu et al., 2004), has revealed that the 3D dynamic flow environment affects bone cell distribution, cell phenotypic expression and mineralized matrix synthesis within tissue-engineered constructs. Such studies are important for the design and optimization of 3D scaffolds suitable in bioreactors for in vitro tissue engineering of bone and stress the need for a proper flow of fluids through the engineered tissue.

Another important problem associated with tissue regeneration in TE is associated with biodegradable scaffolds. Although not exclusively, TE techniques generally involve the use of a temporary biodegradable scaffold that serves as 3D template for initial cell attachment and subsequent tissue formation. The ability of the scaffold to be metabolized by the body allows it to be gradually replaced by new cells to form functional tissues. However, these biodegradable scaffolds also have their downside. Without proper removal of degradation products, accumulation of waste products may impede the growth of the tissue-regenerating cells. This problem can only partially be solved by the use of scaffolds with a slow degradation rate and often requires the use of non-degradable permanent scaffolds.

Thus, in general, cell growth on biodegradable scaffolds requires high levels of mass transfer. Proper growth requires the transfer of sufficient amounts of nutrients and oxygen to the tissues and degraded scaffold mass must be removed. Production of tissue replacements outside the body (ex vivo) is already difficult since conventional bioreactor devices with impeller mixers are often not effective for providing mixing and mass transfer. This challenge arises due to the lack of rapid vascularization (angiogenesis) of large three-dimensional (3-D) scaffold constructs.

SUMMARY OF THEE INVENTION

The present inventors have now found that the above problems in engineered tissue regeneration may be overcome by a further temporal separation of the process of blood vessel ingrowth (vascularization) and the process of tissue ingrowth, and that a reversal of the order in which the scaffold is populated by the various cell types can greatly improve the success and rate of tissue repair.

In a first aspect, the present invention provides a method of treating a tissue defect in a human or animal body comprising the steps of:
 implanting into said body an unseeded scaffold;
 allowing or effecting a wound healing response at the site of said defect;
 allowing said scaffold to be vascularized until a substantially sufficient fluid flow through said scaffold is assured for the transport of nutrients and/or waste products, and
 seeding said vascularised scaffold with a suitable population of tissue-regenerating cells.

An important benefit of this method is that the scaffold may be implanted much earlier than in the prior art methods and the natural wound healing response of the body may optimally be used to increase the rate of vascularization of the scaffold. In contrast, prior art methods do not, or not sufficiently, utilize this response.

In a preferred embodiment of a method of the invention, said tissue defect is a bone defect.

In another preferred embodiment of a method of the invention, said scaffold is a biphasic calcium phosphate (BCP) scaffold.

In yet another preferred embodiment of a method of the invention, said wound healing response is brought about by a wound resulting from a trauma.

It needs to be mentioned that an important advantage of the present invention is that the tissue-regenerating cells can now be introduced at a time in which the body would normally recruit such cells from adjacent tissues or the blood stream.

Preferably thereto, prior to seeding the scaffold with the tissue-regenerating cells, the wound healing response is allowed to proceed or brought about to an extent or level that results in the recruitment of tissue-regenerating cells from the body or the activation of said recruitment. The subsequent seeding may then be regarded as an additional boost of tissue-regenerating cells.

In still another preferred embodiment of a method of the invention, said scaffold comprises angiogenesis stimulating factors selected from the group consisting of angiomotin, vascular endothelial growth factor (VEGF), autotaxin [ATX (NPP-2)], epidermal growth factor (EGF), platelet-derived growth factors (PDGFs), Mts-1 protein; basic fibroblast growth factor (bFGF) or prostatropin; transforming growth factors (TGFs) and nitric oxide (NO).

In a further preferred embodiment of a method of the invention, said scaffold is allowed to be vascularized for a period of between 3 days and 3 months.

In yet a further preferred embodiment of a method of the invention, said tissue-regenerating cells are mesenchymal stem cells.

In still a further preferred embodiment of a method of the invention, said mesenchymal stem cells are induced to form osteoblasts.

In another aspect, the present invention relates to the use of a method of the invention for the reconstruction of bone.

DETAILED DESCRIPTION OF THE INVENTION

Definitions

The headings provided herein are not limitations of the various aspects or embodiments of the invention that can be had by reference to the specification as a whole. Accordingly, the terms defined immediately below are more fully defined by reference to the specification as a whole.

As used herein, the term "tissue" is defined as a coordinated assemblage of one or more types of differentiated cells including, where applicable, their connective tissue and/or mineral matrix, such as, but not limited to, bone tissue, skin tissue, eye tissue, liver tissue, pancreas tissue, blood vessel tissue, ligament tissue, cartilage tissue, muscle tissue and nervous system tissue.

The term "tissue defect", as used herein, is defined as any medical abnormality of a tissue, including, but not limited to, a damaged tissue, a deficient tissue, a degraded tissue, a traumatised tissue. In fact, any abnormality of a tissue that may be regenerated by tissue engineering methods is included in the term "tissue defect".

The term "implanting", as used herein, is used in its art-recognised meaning and is defined as introducing into a body by surgical or non-surgical methods a biological or artificial material, in particular a scaffold material.

The term "scaffold", as used herein, is defined as a biological or artificial tissue engineering carrier matrix for tissue-regenerating cells. A scaffold may be a biocompatible scaffold, a bioactive scaffold and/or a biodegradable scaffold, preferably a biodegradable scaffold. The term scaffold is not limited to any form and may for instance be in the form of a more or less rigid object, or in the form of an amorphous material.

The terms "seeded" and "seeding", as used herein, relate to a partially or essentially completely loaded scaffold, respectively to the process of loading or inoculating a scaffold with tissue-regenerating cells. Seeding may occur onto and/or into a scaffold matrix material. Preferably, seeding is performed by injection of tissue-regenerating cells onto and/or into the scaffold, or by injection of tissue-regenerating cells in peripheral blood vessels allowing "homing" of the cells to the implant site and into and/or onto the scaffold.

The term "tissue-regenerating cells", is used herein to indicate one or more types of cells that may be seeded onto and/or into a scaffold and that are capable of the formation of a coordinated assemblage of one or more types of differentiated cells, optionally including a connective tissue and/or mineral matrix, thereby forming a tissue.

The term "wound healing response", as used herein, is defined as the process associated with the cellular cascades of wound healing that are brought about by injury and the subsequent disturbance of homeostatic events due to, for instance, injury to tissues or organs as a result of implantation of a biomaterial, prosthesis or medical device into a vertebrate body. The response to injury in a vertebrate body is dependent on multiple factors that include the extent of the injury, the loss of basement membrane structures, blood-material interactions, provisional matrix formation, the extent or degree of cellular necrosis, and the extent of the inflammatory response. These events, in turn, may affect the extent or degree of granulation tissue formation, foreign body reaction, and the development of fibrosis or fibrous capsule. Histological features of the granulation tissue include the proliferation of small blood vessels and fibroblasts and, depending on the extent of the injury, granulation tissue may be seen as early as 3 to 5 days following implantation of biomaterial. The volume of implanted biomaterial (size of the defect) will determine the time at which vascularisation has occurred throughout the defect. All above reactions involved in the wound healing process have been described to occur within 2 or 3 weeks of the time of implantation (Anderson, 2000). In relation to bone healing, hemorrage caused by fracture of implantation of a material, results in the formation of a blood clot or haematoma. This clot usually lasts only a few days but it may persist, if extensive, for up to 2 weeks and leads to the development of a fibrin clot (Davies and Hosseini, 2000). Next to ingrowth of sprouting blood vessels, repair cells (mesenchymal stem or progenitor cells) can infiltrate the wound side via this network of fibrin strands. The entire process of wound healing, recruitment of repair cells and vascularisation (angiogenesis) in bone can therefore last from days to weeks or months, depending on the type and size of the defect.

The term "vascularized", as used herein, is defined as comprising microvasculature and microvasculature capable of supporting a supply of blood and/or lymph fluid to the replacement tissue and which vasculature is connected to the vascular circulatory system of the human or animal host. Essentially completely vascularized means that the de novo vasculature is sufficient to support all neotissue.

The term "fluid flow", as used herein, is defined as a flow of blood, lymph and/or other interstitial fluid, preferably blood, in arteries, veins, microvessels and/or interstitial system, in particular in a tissue.

The term "nutrients", as used herein, is defined as comprising essential substances for cellular growth and maintenance, such as oxygen and glucose.

The term "waste products", as used herein, is defined as comprising essential dissimilation products from cellular metabolism, such as carbon dioxide and nitrogen-containing substances, that are to be expelled from the body. Waste products may also include degradation products of biodegradable scaffolds.

Nutritive blood flow in conventional tissue engineering techniques is re-established by the connection of the graft to the vascular system of the recipient by angiogenesis, i.e. the formation of new blood vessels from pre-existing cells in the adjacent microvasculature. Vasculogenesis, i.e. the formation of blood vessels from immature precursor cells comprised in the graft, may also contribute to graft revascularization. It is an aspect of the present invention that this nutritive blood flow is established in a scaffold system in vivo prior to the seeding of the scaffold with tissue-regenerating cells.

As suitable scaffold materials, both organic and inorganic materials, as well as combinations thereof may be used.

Synthetic polymers provide for very suitable organic scaffold materials. Advantages of such polymers include the ability to tailor mechanical properties and degradation kinetics to suit various applications. Synthetic polymers are also attractive because they can be fabricated into various shapes with desired pore morphologic features conducive to tissue in-growth. Furthermore, polymers can be designed with chemical functional groups that can induce tissue in-growth.

Numerous synthetic polymers can be used to prepare synthetic polymer-comprising scaffolds useful in methods of the invention. They may be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif.

Representative synthetic polymers include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyorthoesters, polyphosphazenes, polysiloxanes, polyurethanes, polyvinyl alcohols, polyvinyl esters, polyvinyl ethers, polyvinyl halides, polyvinylpyrrolidone, and blends and copolymers of the above. The scaffold may comprise both oligomers and polymers of the above.

Specific examples of these broad classes of polymers include poly(methyl methacrylate), poly(ethyl methacrylate), poly(butyl methacrylate)) poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly (vinyl chloride), polystyrene, polyurethane, poly(lactic 2( ) acid), poly(butyric acid), poly(valeric acid), poly[lactide-co-glycolide], poly(fumaric acid), poly(maleic acid), copolymers of poly (caprolactone) or poly (lactic acid) with polyethylene glycol and blends thereof.

The polymers used in scaffolds may be non-biodegradable. Examples of preferred non-biodegradable polymers include ethylene vinyl acetate, poly(meth)acrylic acid, polyamides, and copolymers and mixtures thereof.

Polymers used in scaffolds may also be biodegradable. For a detailed review on biodegradable synthetic polymers for tissue engineering, reference is made to the publication by Gunatillake and Adhikari in Cell (Gunatillake A., Adhikari, 2003). The rate of degradation of the biodegradable scaffolds is determined by factors such as configurational structure, copolymer ratio, crystallinity, molecular weight, morphology, stresses, amount of residual monomer, porosity and site of implantation. The skilled person will be able to choose the combination of factors and characteristics such that the rate of degradation is optimized.

Examples of preferred biodegradable polymers include synthetic polymers such as polyesters, polyanhydrides, poly (ortho)esters, polyurethanes, siloxane-based polyurethanes, poly(butyric acid), tyrosine-based polycarbonates, and natural polymers and polymers derived therefrom such as albumin, alginate, casein, chitin, chitosan, collagen, dextran, elastin, proteoglycans, gelatin and other hydrophilic proteins, glutin, zein and other prolamines and hydrophobic proteins, starch and other polysaccharides including cellulose and derivatives thereof (e.g. methyl cellulose, ethyl cellulose, hydroxypropyl cellulose, hydroxy-propyl methyl cellulose, hydroxybutyl methyl cellulose, carboxymethyl cellulose, cellulose acetate, cellulose propionate, cellulose acetate butyrate, cellulose acetate phthalate, cellulose acetate succinate, hydroxypropylmethylcellulose phthalate, cellulose triacetate, cellulose sulphate), poly-1-lysine, polyethylenimine, poly(allyl amine), polyhyaluronic acids, and combinations, copolymers, mixtures and chemical derivatives thereof (substitutions, additions of chemical groups, for example, alkyl, alkylene, hydroxylations, oxidations, and other modifications routinely made by those skilled in the art). In general, these materials degrade either by enzymatic hydrolysis or exposure to water in vivo, by surface or bulk erosion.

The foregoing materials may be used alone, as physical mixtures (blends), or as a co-polymer. The most preferred polymers are polyesters, polyanhydrides, polystyrenes and blends thereof. The polyesters and polyanhydrides are advantageous due to their ease of degradation by hydrolysis of ester linkage, degradation products being resorbed through the metabolic pathways of the body in some cases and because of their potential to tailor the structure to alter degradation rates. Some disadvantages of these polymers in prior art tissue engineering applications are their release of acidic degradation products and its effect on the regenerating tissue. By using a method of the present invention, this disadvantage is essentially overcome. The mechanical properties of the biodegradable material are preferably selected such that early degradation, i.e. degradation prior to sufficient regeneration of the desired tissue, and concomitant loss of mechanical strength is prevented.

Preferred biodegradable polyesters are for instance poly (glycolic acid) (PGA), poly(lactic acid) (PLA), poly(glycolic-co-lactic acid) (PGLA), poly(dioxanone), poly(caprolactone) (PCL), poly(3-hydroxybutyrate) (PHB), poly(3-hydroxyvalerate) (PHV), poly(lactide-co-caprolactone) (PLCL), poly(valerolactone) (PVL), poly(tartronic acid), poly(β-malonic acid), poly(propylene fumarate) (PPF) (preferably photo cross-linkable), poly(ethylene glycol)/poly(lactic acid) (PELA) block copolymer, poly(L-lactic acid-ε-caprolactone) copolymer, and poly(lactide)-poly(ethylene glycol) copolymers.

Preferred biodegradable polyanhydrides are for instance poly [1,6-bis(carboxyphenoxy)hexane], poly(fumaric-co-sebacic)acid or P(FA:SA), and such polyanhydrides may be used in the form of copolymers with polyimides or poly (anhydrides-co-imides) such as poly-[trimellitylimidoglycine-co-bis(carboxyphenoxy)hexane], poly [pyromellityl-imidoalanine-co-1,6-bis(carboph-enoxy)-hexane], poly [sebacic acid-co-1,6-bis(p-carboxyphenoxy)hexane] or P(SA:CPH) and poly[sebacic acid-co-1,3-bis(p-carboxyphenoxy)propane] or P(SA:CPP). Poly(anhydride-co-imides) have significantly improved mechanical properties over polyanhydrides, particularly compressive strengths. Particularly preferred are photo cross-linkable polyanhydrides and copolymers thereof.

Other suitable scaffold materials are biocompatible materials that are accepted by the tissue surface. The broad term biocompatible includes also nontoxicity, noncarcinogenity, chemical inertness, and stability of the material in the living body. Examplary biocompatible materials are titanium, alumina, zirconia, stainless steel, cobalt and alloys thereof and ceramic materials derived therefrom such as $ZrO_2$ and/or $Al_2O_3$. Almost all metallic implants and ceramics are bioinert, meaning that a dense fibrous tissue of variable thickness will encapsulate the scaffold, which prevents proper distribution of stresses and may cause loosening of the implant. Therefore, in specific applications bioactive materials are preferably used. Such materials result in the formation of an interfacial bond between the scaffold and the surrounding tissue.

As examples of inorganic scaffold materials calcium phosphate matrices (CaP) and hydroxyapatite (HA) matrices may be used. CaP, sintered hydroxyapatite and bioactive glasses or ceramics, such as 45S5 Biogilass® (US Biomaterials Corp, USA), and apatite- and wollastonite-containing glass-ceramic (glass-ceramic A-W), that form bone-like apatite on their surfaces in the living body and thereby bond to the living bone, exhibit high bioactivity and biocompatibility and are therefore also very suitable for use in the present invention. Hydroxyapatite has the advantage that it is osteoconductive, which term refers to the materials ability to guide bone formation and bond to bone. A subclass of calcium phosphates which comprise specific arrangements of surface microporosity and micro-architecture have been described as being osteoinductive, which term refers to the materials ability to induce bone cell growth. Very suitable matrix materials are the combined materials such as osteoinductive hydroxyapatite/tricalcium phosphate (HA/TCP) matrices, preferably biphasic calcium phosphate (BCP). A particularly preferred scaffold material in the case of bone regeneration is for instance a biphasic calcium phosphate comprising for instance 60% HA and 40% TCP, with for instance 70% porosity constituted of both microporosity (e.g. 30%-35%<10 μm) and macroporosity (e.g. 50%-55% of 300-600 μm). Examples of commercial BCP with different HA/B-TCP ratios include OsSatura™ (IsoTis OrthoBiologics, Lausanne, Switzerland), MBCP™ (Biomatlante, Nantes, France), Osteosynt® (Einco Biomaterial Ltda, Belo Horizonte, Brazil), Triosite® (Zimmer, Rungis, France) and Ceratite® (Kobayashi Pharmaceutical Co., Ltd., Osaka, Japan).

A disadvantage of these inorganic and ceramic materials is that they are in principle brittle and hence primarily find their application in non-load bearing functions. Such materials may be combined with polymers in order to produce a composite with mechanical properties analogous to bone and a bioactive character. Specifically suitable composite materials are for instance hydroxyapatite coatings on titanium-based implants, layered double hydroxide nanocomposites, HA reinforced with high-density polyethylene, plasma sprayed $HA/ZrO_2$ composite coatings, oxide ceramics with calcium phosphate coatings, glass hydroxyapatite coatings on titanium, and polydimethylsiloxane (PDMS)-$TiO_2$ hybrid optionally treated with hot water.

All of the above scaffold materials may be used in different forms such as in the form of blocks, foams, sponges, granules, cements, implant coatings, composite components and may for instance be combined organic/inorganic materials or ceramics and may be from various origins, natural, biological or synthetic. The various forms may for instance be obtained by extrusion, injection moulding, solvent casting, particular leaching methods, compression moulding and rapid prototyping such as 3D Printing, Multi-phase Jet Solidification, and Fused Deposition Modeling (FDM) of the materials.

A suitable cement may for instance be used as a injectable (bone) scaffold material and may upon hardening and vascularization later be loaded with the cells. Such a cement may for instance comprise hydroxyapatite (HA) microparticles that, depending on their manufacturing method, may either be dense or microporous. A suitable particle size is one in which the particles have a diameter in the range of 10-1000 μm, preferably of 200-300 μm.

The scaffold will generally be implanted by surgery. The surgical procedures to implant the scaffold may be similar to the procedures that are normally used by the skilled surgeon when implanting other types of scaffolds.

It is a feature of the present invention that vascularization of the scaffold material is essentially brought about or at least supported by the normal wound healing response of the body. In this context it should be mentioned that the vascularization, which is brought about by the normal process of wound healing and after which the tissue-regenerating cells are provided to the scaffold, the cells themselves are introduced at a time that the body would normally recruit such cells to start the tissue repair process. Thus, there is a double advantage to the method of the present invention: Firstly, cell survival after implantation is improved due to the fact that vascularization has already occurred, and secondly the cells will be introduced at a time during which the body would normally start to recruit them from surrounding tissues. Thus, the body is already fully geared up to recruitment of cells and repair of tissue and is now provided with an additional source of tissue regenerating cells. Consequently, the provision of tissue regenerating cells can be seen as a booster approach. In order to take full benefit of this effect, it is very suitable that prior to seeding of the tissue regenerating cells, the wound healing response is allowed to progress until the time at which repair cells (e.g. progenitor and stem cells) are recruited for tissue regeneration.

In case of trauma or, more general, injury, the body will naturally induce a wound healing response at the site of the trauma. If, due for instance to immunosuppressive therapy, a wound healing response is not brought about, such a response may be effected, for instance pharmaceutically or by surgical intervention.

Yet, in order to support this natural response, the scaffold material may comprise angiogenesis and vasculogenesis stimulating factors to encourage the formation of new blood vessels from pre-existing cells in the adjacent microvasculature. A number of biomolecules, which induce or promote angiogenesis in tissues may be used to stimulate vascularization of the scaffold material. Representative examples of angiogenesis stimulating factors are angiomotin, vascular endothelial growth factor (VEGF), autotaxin [AIX (NPP-2)], epidermal growth factor (EGF), platelet-derived growth factors (PDGFs), Mts-1 protein (U.S. Pat. No. 6,468,960); basic fibroblast growth factor (bFGF) also called FGF2 or heparin-binding growth factor 2 (hbgf-2) or prostatropin; transforming growth factors (TGFs), nitric oxide (NO), or small-molecular weight peptides derived from the degradation of porcine intestinal submucosa (SIS) (Li et al., 2004). The angiogenesis stimulating factors or angiogenic growth factors may be delivered at the site of required vascularization via direct or sustained release from the scaffold, via delivery of plasmids containing DNA that encodes for angiogenic proteins, or via combined delivery of angiogenic molecules and (blood vessel) endothelial cell transplantation, or via injection in the scaffold prior to implantation or post-implantation.

In another method of supporting the wound healing response, the scaffold may also be seeded with blood-vessel progenitor cells that sprout vessels from within the body of the matrix. This formation of blood vessels from immature precursor cells comprised in the scaffold, may also contribute to scaffold vascularization.

Following its implantation the scaffold is allowed to be vascularized until a substantially sufficient fluid flow through said scaffold is assured for the transport of nutrients and/or waste products. This procedure generally involves closing of the wound after implantation of the scaffold. It should be understood that, when using biodegradable scaffolds, extensive vascularization of non-seeded scaffolds may lead to early scaffold erosion. This should be compensated by optimizing the rate of degradation of the scaffold as described above as well as by optimizing the time of seeding the tissue-regenerating cells. Such optimizations will depend on the size of the scaffold, the type of tissue to be regenerated and the time it takes for the regenerating tissue to produce a connective tissue and/or a mineral matrix that can replace the scaffold's support. In general, for bone regeneration, a vascularization period of 3 days to 3 months provides for sufficient time for the establishment of a flow-through circulation. Normally, after 3 days, initial ingrowth of capillary vessels has occurred to a sufficient degree for the purposes of the invention.

The presence of a substantially sufficient fluid flow through said scaffold for the transport of nutrients and/or waste products may be determined by any method known to the skilled person, such as by ultrasound echoscopy, MRI, or CT scan. In general, fluid flow through a bone structure may be considered "sufeicient" when said fluid flow it is capable of supporting or even stimulating new bone formation, while preventing or even inhibiting bone resorption (see for instance Qin et al., 2003). Thus, the sufficiency of a fluid flow through a scaffold in the context of the present invention may be determined by measuring de novo bone formation rate. However, in the absence of any de novo bone formation, the presence of a substantially sufficient fluid flow may also be inferred from the extent of vascularisation throughout the scaffold or defect. The skilled medical physician is capable of determining, depending on the nature of the defect, the vascularization period allowed, and the size of the scaffold used and the type of tissue treated, when vascularization has progressed to such an extent that a substantially sufficient fluid flow through said scaffold is assured for the transport of nutrients and/or waste products.

The seeding of the vascularized scaffold may be performed with a number of cell types and compositions. A highly preferred seeding comprises undifferentiated progenitor cells, or "stem" cells, for instance stem cells isolated from autologous sources that have been expanded in culture. Preferred progenitor cells are autogenic and allogenic bone marrow derived mesenchymal stem cells (MSC), preferably autogenic MSC. Other suitable progenitor cells are adipose-derived adult stem (ADAS) cells, that are derived from subcutaneous adipose tissue and show characteristics of multipotent adult stem cells. Also foetal stem cells may be used.

For bone regeneration, mesenchymal stem cells harvested from bone marrow may be induced into osteoblasts in vitro, for instance by using dexamethasone. The osteoblasts may be loaded onto the implanted porous scaffolds or may be undergo an additional culture period, for instance of 1-30 days, preferably for about 1-2 weeks before being loaded onto the implanted scaffold. Suitable culture media are known to the skilled person and may for instance comprise glycerophosphate and ascorbic acid. In order to induce in vitro osteogenic differentiation of human MSCs a suitable medium may comprise 1 to 1000 nM dexamethasone (Dex), 0.01 to 4 mM L-ascorbic acid-2-phosphate (AsAP) or 0.25 mM ascorbic acid, and 1 to 10 mM beta-glycerophosphate (beta GP). Optimal osteogenic differentiation, as determined by osteoblastic morphology, expression of alkaline phosphatase (APase), reactivity with anti-osteogenic cell surface monoclonal antibodies, modulation of osteocalcin mRNA production, and the formation of a mineralized extracellular matrix containing hydroxyapatite may for instance be achieved with DMEM base medium supplemented with 100 nM Dex, 0.05 mM AsAP, and 10 mM beta GP. Dulbecco's Modified Eagle's Medium (DMEM) contains 3700 mg/l of sodium bicarbonate and 10 ml/l of 100× antibiotic-antimycotic containing 10 000 units of penicillin (base), 10 000 μg of streptomycin (base) and 25 μg of amphotercin B/mL utilizing penicillin G (sodium salt), streptomycin sulfate, and amphotercin B as Fungizone (D in 0.85% saline.

The skilled person will be able to induce MSC into other cell types and optionally expanded such cells in vitro prior to their seeding on the scaffold. For instance, MSCs may be directed by bone morphogenetic proteins to multiply and become specialized cells that produce cartilage (chondrocytes) or bone (osteoblasts). Under the right set of conditions, MSCs can also be coaxed into forming muscle or tissues that support blood formation or even fat production. In the bone fracture-healing pathway, chondrocytes produce a cartilage framework that is eventually replaced with bone formed by the osteoblasts BMPs may also be incorporated into a scaffold to reproduce the healing cascade at sites that are resistant to normal healing.

Since bone remodeling plays an important role in bone function, bone formation from osteoblasts may be combined with in vivo osteoclastogenesis. For this, MSCs may be differentiated into osteoblasts, seeded on the scaffold and be allowed to mineralize bone. Then, hematopoietic cells may be added to include osteoclastogenesis (see for instance Nakagawa et al. 2004).

The seeding of the vascularized scaffold with a suitable population of tissue-regenerating cells may be performed by injecting the implanted scaffold with any suitable number of cells. Generally, a number of about 1 to 1 million cells per cc of the defect will be applied during seeding. An advantage of performing the seeding with minimal invasive techniques is that minimal additional trauma or injury is exerted on the healing location in the body.

Additionally the healing and regeneration of the tissue defect may be supported by conventional pharmaceuticals, known to the one skilled in the art.

A method for treating a tissue defect according to the present invention may be used in various remodeling and tissue-regeneration applications. For instance, in bone remodeling, a method of the present invention may be applied in defects relating to trauma, orthopedy, tumoral cavities, Ear Nose & Throat, maxillo-facial surgery, peridontal surgery, fractures with bone defects, pseudarthrosis with or without bone defects, vertebral arthrodesis (spinal fusion) and/or tibial osteotomy. Other TE applications may include repair of e.g. bone, cartilage, muscle, tendon/ligament and skin defects.

By way of example, and not of limitation, Examples of the present invention will now be given.

EXAMPLE 1

Effects of Delivering Stem Cells to Existing Subcutaneous Implanted Scaffolds in Nude Mice, Post Implantation Purpose The goal of these experiments is to determine the difference between the bone forming capacity of adult, bone marrow derived stem cells applied to scaffolds prior to subcutaneous implantation versus stem cells injected subcutaneously at a later stage onto already vascularised implanted scaffolds.

Experimental Design:

In this study, a total of 12 nude mice are used (3 per time period) with 4 implantation sites each. Next to a negative control (control scaffold material (biphasic calcium phosphate—BCP) and a positive control (BCP with cells added at time of implantation (t=0), there are 4 experimental groups:
(1) BCP with cells added postoperatively at day 3,
(2) BCP with cells added post-operatively at day 7,
(3) BCP with cells added post-operatively at day 14, and
(4) BCP with cells added post-operatively at day 21.

The experiment is set-up as such that each mouse will contain one negative control implant (without cells), one positive control implant (to which cells have been added per-operatively), and two implants to which cells have been added (injected) after the specified time periods of either 3 days, 1, 2 or 3 weeks post-implantation. Below table shows the experimental design of the study:

| Mouse 1-4 | 6 weeks + 3 days survival time | 7 weeks survival time | 8 weeks survival time | 9 weeks survival time |
|---|---|---|---|---|
| Pocket 1 | BCP + cells | BCP + cells | BCP + cells | BCP + cells |
| Pocket 2 | BCP no cells | BCP no cells | BCP no cells | BCP no cells |
| Pocket 3 | BCP + cells after 3 days | BCP + cells after 1 week | BCP + cells after 2 weeks | BCP + cells after 3 weeks |
| Pocket 4 | BCP + cells after 3 days | BCP + cells after 1 week | BCP + cells after 2 weeks | BCP + cells after 3 weeks |
| Total cells needed for 3 mice in each time point | 5 million Time 0 10 million Time 2 w | 5 million Time 0 10 million Time 7 w | 5 million Time 0 10 million Time 8 w | 5 million Time 0 10 million Time 9 w |

Materials:

Biphasic calcium phosphate scaffolds comprising 80% hydroxyapatite and 20% beta-tricalcium phosphate are used as scaffolds. The materials are sintered at 1200 degrees Celsius for 8 hours and have an average macropore size of 400 micrometers. The materials are implanted in the form of irregular chips measuring 2-5 mm in diameter.

Expanded frozen goat bone marrow stem cells from other studies will be used. The number of cells needed for t=0 is 20 million, and the number of cells needed for each of the four experimental time points is 6.4 million cells, respectively. A total number of 60 million goat bone marrow derived stem cells is therefore needed divided over 5 separate cryopreservation vials; one with 20 million cells and four with 10 million cells.

Methods:

Thaw goat bone marrow cells and culture 6 culture flasks having a surface of 420 cm$^2$ (T420's) until confluent. Freeze cells.

After thawing, seed 1.6 million cells on scaffolds 2 hours prior to implantation as a positive control Negative control: BCP with no cells Implant two pockets with BCP for subsequent injection of cells after listed time points 3 days, 1 week, 2 weeks, 3 weeks after implantation of scaffolds subcutaneously inject 1.6 million cells in 0.2 cc saline on top of scaffolds Explant mice 6 weeks from time of subcutaneous injections Evaluation:

After the respective implantation times, all samples will be retrieved from the mice and they will be process for undecalcified histology. The presence of de novo bone formation will be qualitatively evaluated by light microscopy.

REFERENCES

Anderson J M. 2000. The cellular cascades of wound healing, in: Bone Engineering, J E Davies (ed), em squared incorporated, Toronto, Canada, p. 81-93.

Davies and Hosseini. 2000. Histodynamics of endosseous wound healing, J E Davies (ed), em squared incorporated, Toronto, Canada, p. 1-14.

Gunatillake A., Adhikari R. 2003. Biodegradable synthetic polymers for tissue engineering. European Cells and Materials Vol. 5:1-16.

Hillsley M V, Frangos J A. 1994. Bone tissue engineering: the role of interstitial fluid flow. Biotechnol Bioeng. 43(7): 573-81.

Li F, Li W, Johnson S, Ingram D, Yoder M, Badylak S. 2004. Low-molecular-weight peptides derived from extracellular matrix as chemoattractants for primary endothelial cells. Endothelium. 11(3-4):199-206.

Nakagawa K, Abukawa H, Shin MY, Terai H, Troulis M J, Vacanti J P. 2004. Osteoclastogenesis on tissue-engineered bone. Tissue Eng. 10(1-2):93-100.

Qin Y-X, Kaplan T, Saldanha A, Rubin C. 2003. Fluid pressure gradients, arising from oscillations in intramedullary pressure, is correlated with the formation of bone and inhibition of intracortical porosity. *Journal of Biomechanics* 36:1427-1437

Yu X, Botchwey E A, Levine E M, Pollack S R, Laurencin C T. 2004. Bioreactor-based bone tissue engineering: the influence of dynamic flow on osteoblast phenotypic expression and matrix mineralization. Proc Natl Acad Sci USA. 101(31):11203-8.

The invention claimed is:

1. A method of treating a tissue defect in a human or animal body comprising the steps of implanting into said body an unseeded scaffold, wherein said scaffold is a biphasic calcium phosphate (BCP) scaffold; allowing or effecting a wound healing response at the site of said defect; allowing said scaffold to be vascularized until a substantially sufficient fluid flow through said scaffold is assured for the transport of nutrients and/or waste products, and seeding said vascularized scaffold with a suitable population of tissue-regenerating cells.

2. Method according to claim 1, wherein said tissue defect is a bone defect.

3. Method according to claim 1, wherein said wound healing response is brought about by a wound resulting from a trauma.

4. Method according to claim 1, wherein said wound healing response results in the recruitment of tissue-regenerating cells from the body.

5. Method according to claim 1, wherein said scaffold is allowed to be vascularized for a period of between 3 days and 3 months.

6. Method according to claim 1, wherein said tissue-regenerating cells are mesenchymal stem cells.

7. Method according to claim 6, wherein said mesenchymal stem cells are induced to form osteoblasts.

8. Method according to claim 1, which results in the reconstruction of bone.

* * * * *